United States Patent [19]

Fedotov et al.

[11] 4,162,678
[45] Jul. 31, 1979

[54] SURGICAL APPARATUS FOR SIMULTANEOUS RESECTION OF SOFT TISSUES AND THEIR SUTURING WITH METAL STAPLES

[75] Inventors: Vladimir M. Fedotov; Boris A. Smirnov; Valery V. Revo; Sergei N. Lapchenko, all of Moscow, U.S.S.R.

[73] Assignee: Vsesojuzny Nauchno-Issledovatelsky I Ispytatelny Institut Meditsinskoi Tekhniki, U.S.S.R.

[21] Appl. No.: 843,706

[22] Filed: Oct. 13, 1977

[30] Foreign Application Priority Data

Dec. 17, 1976 [SU] U.S.S.R. .................................. 2430153

[51] Int. Cl.² ..................................................... A61B 17/32
[52] U.S. Cl. .................................. 128/305; 128/334 R; 227/19; 227/21; 227/25; 227/65; 227/76; 128/325
[58] Field of Search ............... 128/334 R, 334 C, 335, 128/305, 346; 227/19, 21, 25, 65, 76

[56] References Cited

U.S. PATENT DOCUMENTS

| | | |
|---|---|---|
| 2,344,071 | 3/1944 | Wilson et al. ............................ 227/19 |
| 2,684,070 | 7/1954 | Kelsey ...................................... 128/337 |
| 3,079,606 | 3/1963 | Bobrov et al. .......................... 227/19 |
| 3,317,105 | 5/1967 | Astaljev et al. ................... 128/334 R |
| 4,014,492 | 3/1977 | Rothfoss .................................. 227/19 |

FOREIGN PATENT DOCUMENTS 456458  11/1936  United Kingdom ...................... 128/337

*Primary Examiner*—Robert W. Michell
*Assistant Examiner*—C. W. Shedd
*Attorney, Agent, or Firm*—Steinberg & Blake

[57] ABSTRACT

A surgical apparatus for the simultaneous resection of soft tissues and their suturing with metal staples comprises an anvil and a staple branches, hinge-connected and having longitudinal jaws situated one opposite the other. A longitudinal row of grooves is made on the jaw of the anvil branch for clinching the ends of staples, while slots for the staples with staple tappets placed therein are provided on the jaw of the staple branch opposite said grooves. A plank with a wedge bevel on its end intended for interaction with the staple tappets when ejecting the staples is situated in the slot of the staple branch, and is longitudinally movable therealong. Rotation shafts are set along each branch with needles set perpendicularly to them, intended for grasping the soft tissue. Rigidly secured on the shafts are cranks, movably connected through a link so that when the branches are being drawn together, this provides for the rotation of the shafts with the needles towards each other, resulting in the portion of the soft tissue, grasped by the needles, being forced into the clearance between the branches with the formation of a roll of soft tissue intended for excision. Situated on the staple branch is a blade for excising said roll of soft tissue, longitudinally movable together with the plank actuating the staple tappets.

The apparatus makes it possible to separate a blood-supplied graft of soft tissue or remove an area of soft tissue with the simultaneous suturing of the wound therebeneath, providing for minimum loss of blood and reducing the time of the operation.

2 Claims, 7 Drawing Figures

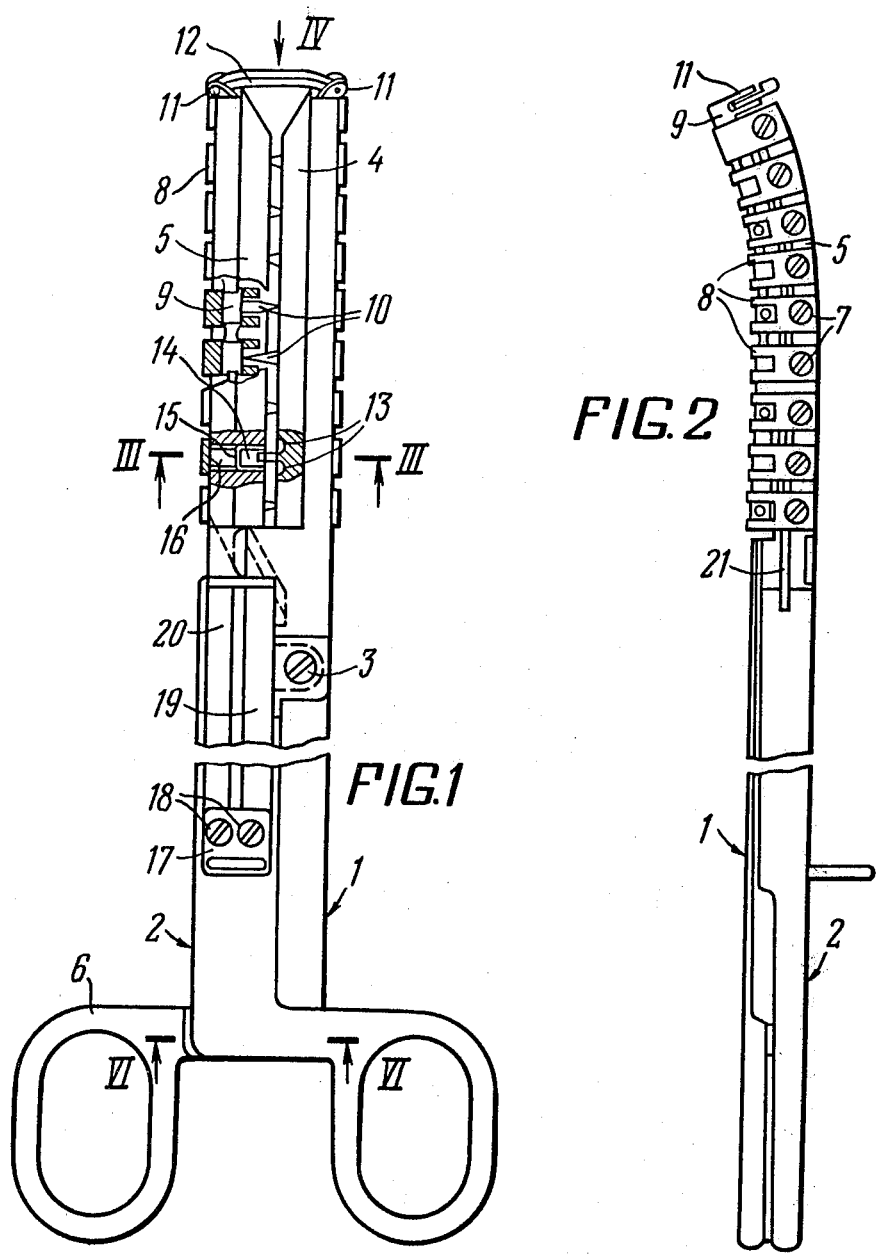

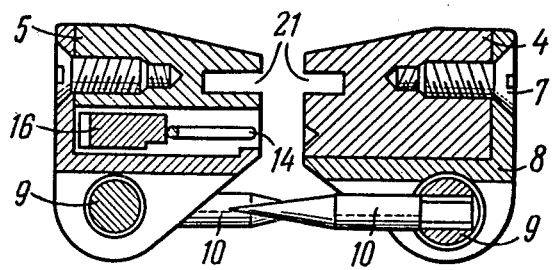
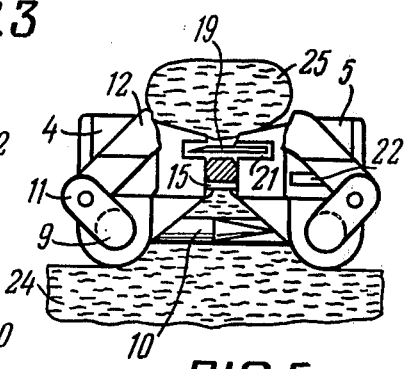
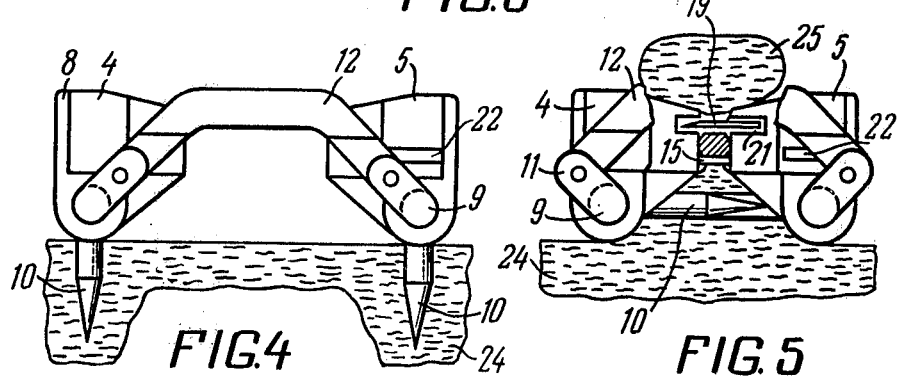
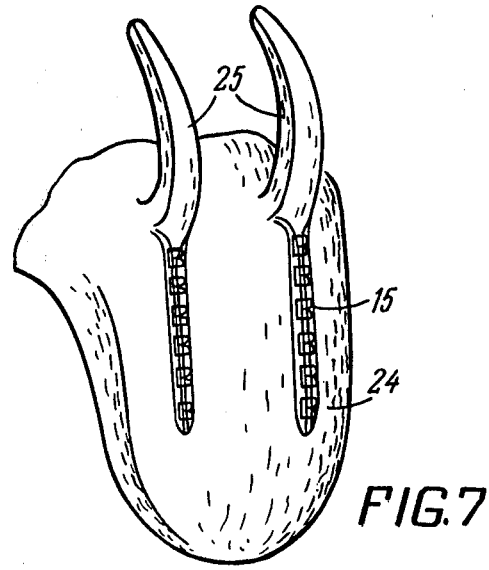
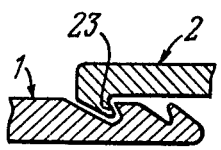

SURGICAL APPARATUS FOR SIMULTANEOUS RESECTION OF SOFT TISSUES AND THEIR SUTURING WITH METAL STAPLES

The proposed invention relates to medical equipment, and more particularly to surgical apparatus for the suturing of soft tissues with metal staples with their simultaneous excision along the suture, and can be used for resecting portions or organs with the suturing of the remaining part of an organ, for example, the stomach or other organs. The proposed apparatus can be most advantageously used in otorhinolaryngology for obtaining blood-supplied lingual tissue flaps for voice-restoration surgery.

Known in the art is a surgical apparatus for the simultaneous resection of soft tissues and their suturing usually employed for gastro-intestinal anastomoses. This apparatus comprises hinge-connected anvil and staple branches with longitudinally situated jaws opposite one another. Made in the jaw of the anvil branch is a longitudinal row of grooves for clinching the ends of the staples. Situated on the jaw of the staple branch is a staple magazine with slots containing staples and staple tappets opposite said grooves. A plank with a wedge-like bevel end facing the staple tappets and intended for interaction with said tappets for ejecting said staples is situated in the longitudinal slot of the staple branch and is movable along it. Also accommodated in the staple branch is a blade for dissecting the tissue, movable longitudinally together with the plank, and a latch for locking the branches in a position in which they are drawn close together up to the suturing clearance.

The prior art apparatus is mainly intended for placing lateral interintestinal anastomoses and operates in the following way. The jaws of the branches are inserted into the lumen of the intestines to be sutured through an opening in the walls of said intestines, and the intestinal walls to be sutured are placed between the jaws in the open position.

The branches are then hinged together, and, by a reciprocal rotation of the anvil and the staple branches, their jaws are drawn close together up to the suturing clearance and locked by means of the latch.

The plank with the blade is moved in the direction of the longitudinal jaws. The wedge-like bevel of the plank actuates the staple tappets, moving them along the staple slots. Upon their motion, the tappets eject the staples out of the staple slots. Upon their emergence from the staple slots, the ends of the staples pierce the tissue and, coming against the grooves in the anvil branch, are clinched in a B-shaped manner, firmly joining the tissues.

Simultaneously, the advancing blade dissects the tissue between the sutures. Suturing being over, the anvil and staple branches are unlocked, and the apparatus is removed from the site of the sutures. The walls of the intestines are sutured and a lumen has been formed between them, ensuring patency of the intestine. The openings in the intestinal walls left after the withdrawal of the longitudinal jaws are sutured by hand.

The longitudinal jaws of this apparatus provide free access to the operating area under conditions of a narrow operating field, particularly, in the mouth cavity near the larynx.

This apparatus, however, does not provide for detaching a flap-like area of soft tissues from the surface of an organ, since the surface of the tissue situated between the jaws slips over the surface of the jaws without being secured thereon.

For this reason, the prior art apparatus cannot be used, for example, for obtaining a flap-like blood-supplied graft of the soft lingual tissue and simultaneous suturing of the wound under the flap during an operation for voice restoration, requiring the replacement of removed throat tissue affected by a malignant tumour with the healthy soft tissue of another organ.

At present, the necessary flap graft is obtained during surgery for voice restoration and the wound under the flap is sutured by hand, which, under conditions of a narrow operating field, takes a long time (3–4 hours) and entails heavy loss of blood.

It is an object of the present invention to provide a surgical apparatus for simultaneous resection of soft tissues and their suturing with metal staples, that would provide, at the same time, for the separation of a flap graft of soft tissue on the surface of an organ, including a blood-supplied one, and the suturing of the wound beneath the flap, allowing to considerably reduce blood loss, to speed up and simplify surgery.

This object is achieved by that in a surgical apparatus for the resection of soft tissues and their suturing with metal staples, comprising hinge-connected elongated anvil and staple branches with longitudinal jaws situated opposite each other, and the jaw of the anvil branch having a longitudinal row of grooves for clinching the staple ends, with the jaw of the staple branch having, opposite said grooves, slots with staple tappets, and also a plank with a wedge-like bevel at the end incorporated in the longitudinal slot of the staple branch, movable along said slot, the bevel facing the jaw and intended for interaction with the staple tappets for ejecting said staples, and a blade for cutting off a tissue flap situated in the staple branch and movable longitudinally together with the plank, and further having a clamp for locking the branches in a position whereby they are brought close together up to the suturing clearance, and, according to the invention, there are rotation shafts set along each of the branches with rows of needles secured thereon perpendicularly to said shafts for grasping the soft tissues, and cranks rigidly secured on the ends of the shafts which are brought closer together in the process of drawing the branches together, the ends of said cranks being movably connected with a link, so that when the branches are drawn together the shafts with the needles rotate towards each other, which results in forcing the area of soft tissue grasped by the needles into the clearance between the branches, with the formation of a roll of soft tissue intended for excision.

The proposed surgical apparatus, under conditions of a narrow operating field, provides for quickly and easily separating the required soft tissue flap graft, while simultaneously suturing up the wound beneath the flap, which cuts operation time 5–7 times. The proposed apparatus for the first time solves the problem of obtaining blood-supplied soft tissue grafts on organs with an ample network of blood vessels, ensuring the minimal loss of blood, which allows using the apparatus when grafting lingual tissue flaps for voice restoration surgery in otorhinolaryngology. The apparatus may find wide application for the performance of various operations in plastic and restorative surgery.

The design of the apparatus is simple and reliable and is readily comprehensible to the surgeon.

It is expedient that the rotation shafts be made flexible and the jaws of the branches be arched.

Such an embodiment of the longitudinal jaws of the apparatus makes it much easier to obtain the required soft tissue flap grafts on the arch-like surface of an organ like, say, the tongue, in its root portion near the larynx.

The invention will now be described with reference to the accompanying drawings, wherein:

FIG. 1 is a top view of a surgical apparatus for the simultaneous resection of soft tissues and their suturing with metal staples, according to the invention;

FIG. 2 is a side view of the apparatus of FIG. 1;

FIG. 3 is a section view along line III—III of FIG. 1, on an enlarged scale;

FIG. 4 is a view taken along arrow IV of FIG. 1, on an enlarged scale, with the jaws of the branches drawn apart and the needles piercing soft tissue;

FIG. 5 is a similar view with the jaws of the branches drawn together up to the suturing clearance, with an excised portion of soft tissue and the sutured wound therebeneath;

FIG. 6 is a section view along line VI—VI of FIG. 1;

FIG. 7 shows the tongue with two flap grafts and the wounds beneath them sutured with the aid of the apparatus, according to the invention.

The surgical apparatus for the simultaneous resection of soft tissue and their suturing with metal staples comprises an elongated anvil branch 1 and a staple branch 2 (FIGS. 1 and 2), which are hinged-connected by means of screw 3, have longitudinal jaws 4 and 5 (FIG. 1), and are provided with rings 6 for holding the apparatus. Holders 8 are secured with screws 7 on the jaws 4 and 5 (FIG. 3), holding rotation shafts 9 with needles 10 set perpendicularly to the shafts 9. The longitudinal jaws 4 and 5 are arched, as shown in FIG. 2, and the rotation shafts 9 are made flexible. The rotation shafts 9 have on their ends, drawn together in the process of drawing together, the branches 1 and 2, cranks 11 by means of which they are movably connected through a link 12 (FIGS. 1 and 4). Situated on the longitudinal jaw 4 (FIG. 1) of the anvil branch 1 is a longitudinal row of grooves 13, while the longitudinal jaw 5 of the staple branch 2 has slots 14 situated opposite the grooves 13 and intended for U-shaped staples 15 and staple tappets 16. On the staple branch 2, there is a thumbpiece 17 secured to which with screws 18 are a blade 19 and a plank 20 with a wedge-like bevel facing the jaw 5 and movable within longitudinal slots 21 and 22 (FIG. 5). When drawn apart and when drawn together, with the anvil branch 1 (FIG. 1) and the staple branch 2 brought up to the suturing clearance, the branches 1 and 2 are locked by means of a rack clamp 23 (FIG. 6).

We shall now illustrate the operation of a surgical apparatus according to the invention, by way of an example of separating a lingual soft tissue flap graft and of suturing the wound beneath the flap.

The apparatus with the branches 1 and 2 drawn apart, with the needles 10 (FIG. 4) on the rotation shafts 9 situated perpendicularly to the surface of the lingual tissue 24 to be grafted, is pressed with the surface of the longitudinal jaws 4 and 5 with the needles 10, against the portion of the soft tissue from which it is desired to obtain a flap graft, during which the needles 10 pierce the soft tissue. The rings 6 (FIG. 1) are drawn together until the anvil 1 and staple 2 branches are locked by the rack clamp 23 (FIG. 6). At the moment when the branches 1 and 2 are being drawn together, the link 12 (FIG. 5), its ends thrust against the cranks 11, creates a rotating moment on the rotation shafts 9 with the needles 10, and they turn towards each other. As a result of the needles 10 turning towards each other, the flap-like portion 25 of soft tissue, situated between the longitudinal jaws 4 and 5, is forced into the clearance between the branches 1 and 2 (FIG. 1), forming a roll of soft tissue intended for excision. By moving the thumbpiece 17 with the blade 19 and the plank 20 along the staple branch 2 towards the longitudinal jaws 4 and 5, the area 25 (FIG. 5) of the soft tissue in the shape of a flap is excised to the full length of the longitudinal jaws 4 and 5, simultaneously with the suturing of the wound beneath the flap with the staples 15. Then the rings 6 (FIG. 1) are drawn apart into the initial position and the apparatus is removed.

Thereupon, from the portion 25 of soft tissue on the surface of the tongue 24 (FIG. 7), there is formed a flap graft on a pedicle for the preservation of its blood supply, and the wound beneath it is sutured with the staples 15. The second graft is obtained in the same way.

The apparatus makes it possible to perform operations for the complete removal of affected areas from the surface of soft tissues of organs with the suturing of the wound beneath them. This is achieved by the needles 10 (FIG. 5), situated in the middle part of the jaws 4 and 5 are made longer than the needles 10 situated at the ends of the jaws 4 and 5, enabling to increase the depth of grasping the soft tissue situated between the middle parts of the jaws 4 and 5, while reducing this depth to the minimum at the ends of the jaws 4 and 5.

What is claimed is:

1. A surgical apparatus for the simultaneous resection of soft tissues and their suturing with metal staples, comprising: an elongated anvil branch; an elongated staple branch hinge-connected with said anvil branch; a jaw on each said branch; the jaw of the anvil branch being situated opposite the jaw of the staple branch; said anvil branch being provided with a longitudinal row of grooves for clinching the ends of staples; said staple branch having slots for the staples situated opposite said grooves, and a longitudinal slot; staple tappets housed in said staple slots; a plank situated in said longitudinal slot of the staple branch and movable therealong; a wedge bevel at the end of said plank, facing the jaw and intended for interacting with said staple tappets when ejecting the staples; a clamp for locking the branches in a position when they are drawn together up to the suturing clearance; two rotation shafts, each of which is set along one of said branches; needles for grasping soft tissue, secured on said rotation shafts substantially perpendicularly to the latter; cranks rigidly secured on said rotation shafts so that upon drawing the branches together the rotation of said shafts with the needles towards each other is ensured, resulting in the areas of soft tissue grasped by the needles being forced into the clearance between the branches, with the formation of a roll of soft tissue intended for excision; a blade for excising said roll of soft tissue situated in said staple branch, longitudinally movable together with said plank.

2. A surgical apparatus as claimed in claim 1, in which said rotation shafts are made flexible and the jaws of said branches are arched.

* * * * *